(12) United States Patent
Tashiro et al.

(10) Patent No.: US 7,563,022 B2
(45) Date of Patent: Jul. 21, 2009

(54) METHODS AND APPARATUS FOR INSPECTING REACTOR PRESSURE TUBES

(75) Inventors: Kelvin Tashiro, Guelph (CA); John H. Sedo, Aurora (CA); Mario Ng, Markham (CA)

(73) Assignees: Ontario Power Generation Inc., Toronto, Ontario (CA); Kinetrics, Inc., Toronto, Ontario (CA)

( * ) Notice: Subject to any disclaimer, the term of this patent is extended or adjusted under 35 U.S.C. 154(b) by 590 days.

(21) Appl. No.: 10/995,085

(22) Filed: Nov. 22, 2004

(65) Prior Publication Data

US 2005/0220252 A1   Oct. 6, 2005

Related U.S. Application Data

(60) Provisional application No. 60/525,121, filed on Nov. 28, 2003.

(51) Int. Cl.
*G01K 1/10* (2006.01)
*G01K 13/04* (2006.01)
*G01K 7/02* (2006.01)
*G01N 25/00* (2006.01)
*G01N 25/18* (2006.01)

(52) U.S. Cl. .......................... 374/147; 374/45; 374/57; 374/4; 374/185; 374/179

(58) Field of Classification Search .............. 374/4–7, 374/43–45, 57, 29–30, 137, 141–143, 163, 374/183, 185, 179, 112, 114, 156, 159, 16, 374/100, 27; 376/245–254, 260; 422/53; 436/6

See application file for complete search history.

(56) References Cited

U.S. PATENT DOCUMENTS 2,753,281 A * 7/1956 Scaff et al. .................. 117/74

2,842,438 A * 7/1958 Saarivirta et al. ............ 420/492

(Continued)

FOREIGN PATENT DOCUMENTS

CA    1 173 569    8/1984

(Continued)

OTHER PUBLICATIONS

R.A. Finch, et al. "Apparatus for Determining Thermophysical Properties of Solids by Direct Electrical Pulse Heating." Review of Scientific Instruments. vol. 40, No. 9 (Sep. 1969) pp. 1195-1199.

(Continued)

*Primary Examiner*—Gail Verbitsky
(74) *Attorney, Agent, or Firm*—Patterson & Sheridan, L.L.P.

(57) ABSTRACT

An apparatus and method for determining terminal solid solubility temperature in materials capable of forming hydrides, such as reactor pressure tubes. An inspection device is positioned within the reactor pressure tube under test and a pair of annular seals are radially deployed to seal a section of the pressure tube. Any water within the sealed section is displaced through the injection of gas and the heating of the sealed section to dry the tube and the device. A probe assembly on the device is deployed to contact the interior surface of the pressure tube and measure resistivity changes in the pressure tube wall as a function of temperature. The probe assembly includes a thermocouple probe for measuring temperature and transmit and receive coils for inducing eddy currents within the pressure tube wall. The pressure tube is allowed to cool at a predetermined rate, is reheated at a predetermined rate, and is allowed to cool again. Discontinuities within the temperature coefficient of resistivity indicate terminal solid solubility temperatures of precipitation or dissolution, which may be used to determine the hydrogen concentration of the sealed section of reactor pressure tube.

13 Claims, 10 Drawing Sheets

U.S. PATENT DOCUMENTS

| | | | | |
|---|---|---|---|---|
| 3,368,389 A * | 2/1968 | Barnett | ............... | 73/64.54 |
| 3,440,140 A * | 4/1969 | Sawatzky | ............. | 376/305 |
| 3,575,806 A * | 4/1971 | Boulton | ............. | 376/305 |
| 3,619,771 A | 11/1971 | Hentschel | | |
| 3,635,769 A * | 1/1972 | Shaw | ............... | 148/423 |
| 3,651,398 A | 3/1972 | Urmenyl | | |
| 3,732,074 A * | 5/1973 | Feilter et al. | ............ | 436/6 |
| 3,918,300 A * | 11/1975 | Weisstuch et al. | ........ | 73/112 |
| 3,945,245 A | 3/1976 | Stehle et al. | | |
| 4,073,427 A * | 2/1978 | Keifert et al. | ........... | 228/165 |
| 4,303,884 A | 12/1981 | Malick | | |
| 4,396,300 A * | 8/1983 | Characklis et al. | ......... | 374/43 |
| 4,452,648 A * | 6/1984 | Cheadle et al. | ........ | 148/672 |
| 4,508,129 A | 4/1985 | Brown | | |
| 4,510,178 A * | 4/1985 | Paulson et al. | ........ | 29/610.1 |
| 4,667,149 A | 5/1987 | Cohen et al. | | |
| 4,668,912 A | 5/1987 | Junker | | |
| 4,834,807 A * | 5/1989 | Burley | ............. | 428/457 |
| 4,893,079 A | 1/1990 | Kustra et al. | | |
| 4,922,201 A | 5/1990 | Vernon et al. | | |
| 4,988,210 A * | 1/1991 | Koshihara et al. | ........ | 374/5 |
| 5,250,776 A | 10/1993 | Pfaffmann | | |
| 5,256,966 A * | 10/1993 | Edwards | ............. | 324/220 |
| 5,260,218 A * | 11/1993 | Garde | ............. | 436/6 |
| 5,307,385 A * | 4/1994 | Shimanuki et al. | ...... | 376/249 |
| 5,668,301 A | 9/1997 | Hunter | | |
| 5,776,266 A * | 7/1998 | Tobin | ............. | 148/277 |
| 6,051,972 A | 4/2000 | Bour et al. | | |
| 6,192,098 B1 * | 2/2001 | Van Swam | ............ | 376/417 |
| 6,241,383 B1 * | 6/2001 | Feller et al. | ............ | 374/40 |
| 6,339,327 B1 * | 1/2002 | Potiquet et al. | ........ | 324/220 |
| 6,365,476 B1 * | 4/2002 | Talwar et al. | ............ | 438/308 |
| 6,386,272 B1 * | 5/2002 | Starner et al. | ............ | 165/11.1 |
| 6,456,066 B1 | 9/2002 | Burd et al. | | |
| 6,541,964 B1 | 4/2003 | Jourdain et al. | | |
| 6,583,618 B2 | 6/2003 | McClelland | | |
| 6,714,018 B2 * | 3/2004 | Bass | ............. | 324/525 |
| 7,048,844 B2 * | 5/2006 | Chen et al. | ............ | 205/789.5 |
| 7,077,563 B2 * | 7/2006 | Xiao et al. | ............ | 374/29 |
| 7,375,013 B2 * | 5/2008 | Yamamoto et al. | ........ | 438/583 |
| 2002/0027437 A1 | 3/2002 | Tasca | | |
| 2003/0185333 A1 * | 10/2003 | Sacedon Adelantado et al. | ............ | 376/245 |
| 2006/0256834 A1 * | 11/2006 | Chang et al. | ............ | 374/5 |
| 2009/0011148 A1 * | 1/2009 | Rajagopalan et al. | ...... | 427/577 |
| 2009/0052497 A1 * | 2/2009 | Tipler | ............ | 374/141 |

FOREIGN PATENT DOCUMENTS

| | | | |
|---|---|---|---|
| JP | 57-052857 | | 3/1982 |
| JP | 60-042647 | | 6/1985 |
| JP | 01155910 A | * | 6/1989 |
| JP | 06281555 A | * | 10/1994 |
| JP | 09-318570 | | 12/1997 |
| JP | 10147850 A | * | 6/1998 |

OTHER PUBLICATIONS

T. Sakai, et al. "A Resistimetric Study of the Precipitation of Hydrides in Unalloyed and Alloyed Zirconium." Transactions of the Japan Institute of Metals. vol. 14, No. 3 (May 1973) pp. 194-198.

J. L. Sacedon, et al. "A new method to study hydriding processes from the inner surfaces of fuel cladding." Journal of Nuclear Materials. vol. 327 (Apr. 2004) pp. 11-18.

* cited by examiner

METHODS AND APPARATUS FOR INSPECTING REACTOR PRESSURE TUBES

CROSS REFERENCE TO RELATED APPLICATION

This application claims priority from U.S. patent application No. 60/525,121 filed Nov. 28, 2003, which is pending.

FIELD OF THE INVENTION

This invention relates to the measurement of terminal solid solubility (TSS) temperature in alloys capable of forming hydrides.

BACKGROUND OF THE INVENTION

Ensuring the structural integrity of pressure tubes in nuclear reactors presents a continuous problem for safety analysts.

Pressure tubes serve as the high pressure boundary of the reactor core. Over time, with normal operation, the pressure tube corrodes, resulting in the absorption of hydrogen isotopes in the material. The hydrogen isotopes then can form solid hydrides in the matrix. These hydrides are particularly brittle and can compromise the structural integrity of the pressure tube. A pressure tube with a significant concentration of hydrides present at operating conditions is at risk of hydride cracking.

Accordingly, it is important to monitor the concentration of hydrides within the pressure tube material at operating conditions.

One method of determining the concentration of hydrides is to obtain a scrape sample from the interior of the pressure tube during a shutdown. The concentration of hydrides can be determined using an appropriate Arrhenius relationship if the concentration of hydrogen is known. The sample can be analyzed by chemical methods to determine the concentration of hydrogen.

Drawbacks of the scrape method include the delay occasioned in shipping a sample to a testing laboratory and awaiting the results, the radiation risks from handling a sample from within the pressure tube, the chance of sample contamination in handling and transit, the limitation of the sampling to the surface of the tube interior, and the inability to re-sample the same area of the tube again.

Other applications also employ materials that form hydrides and that may suffer from deterioration due to the formation of hydrides. Some of these applications involve material located in hazardous environments or environments that are difficult to access. Accordingly, it would be advantageous to have a device and method for inspecting such material.

SUMMARY OF THE INVENTION

The present invention provides a method and an apparatus for indirectly determining the terminal solid solubility (TSS) temperature for reactor pressure tubes without the necessity of extracting a sample from the interior wall of the tube. The method and the apparatus measure the terminal solid solubility (TSS) temperature at which hydrides precipitate or dissolve. Having determined the TSS temperature, one might thereafter determine the hydride concentration using an appropriate Arrhenius relationship. The method and apparatus employ eddy currents to measure the temperature coefficient of resistivity for the pressure tube material over a specified temperature range. A discontinuity in the temperature coefficient of resistivity identifies a TSS temperature of precipitation or dissolution.

In one aspect, the present invention provides a method of inspecting reactor pressure tubes. The method includes the steps of sealing a section of the reactor pressure tube, initiating a temperature change within the reactor pressure tube at a predetermined rate, measuring changes in the resistivity of the reactor pressure tube in relation to the temperature change, and calculating the TSS temperature from the measured changes in resistivity.

In another aspect, the present invention provides an inspection device for inspecting reactor pressure tubes. The device includes a device body, deployable seals mounted on the device body for sealing a section of the reactor pressure tube, a heater for controlling a temperature change within the reactor pressure tube at a predetermined rate, and a probe assembly for measuring changes in the resistivity of the reactor pressure tube in relation to the temperature change.

In a further aspect, the present invention provides a method of determining the TSS temperature within a material, the material being an alloy capable of forming hydrides. The method includes the steps of sealing a section of the material, initiating a temperature change within the material at a predetermined rate, measuring changes in the resistivity of the material in relation to the temperature change, and calculating the TSS temperature from the measured changes in electrical resistivity.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Reference will now be made, by way of example, to the accompanying drawings which show an embodiment of the present invention, and in which.

Similar numerals are used in different figures to denote similar components.

DESCRIPTION OF SPECIFIC EMBODIMENTS

The concentration of hydrides at operating conditions may be determined by measuring the concentration of hydrogen.

The concentration of hydrogen can be found through measuring the temperatures at which hydrides dissolve or precipitate in the matrix. These temperatures are known as the Terminal Solid Solubility (TSSd) temperature of dissolution and the TSSp temperature of precipitation. TSS relates the solid solution concentration of hydrogen as a function of temperature in an alloy. It also relates the presence or absence of hydrides at a given temperature and overall hydrogen concentration. Using an appropriate Arrhenius relationship, the measurement of TSSd or TSSp leads to an assessment of hydrogen concentration in a reactor pressure tube.

The TSSd temperature marks the temperature at which all hydrides in the matrix will be completely dissolved on heating. The TSSp is lower than the TSSd for a zirconium matrix, and marks the temperature at which hydrides will begin to precipitate on cooling.

Figure 10:
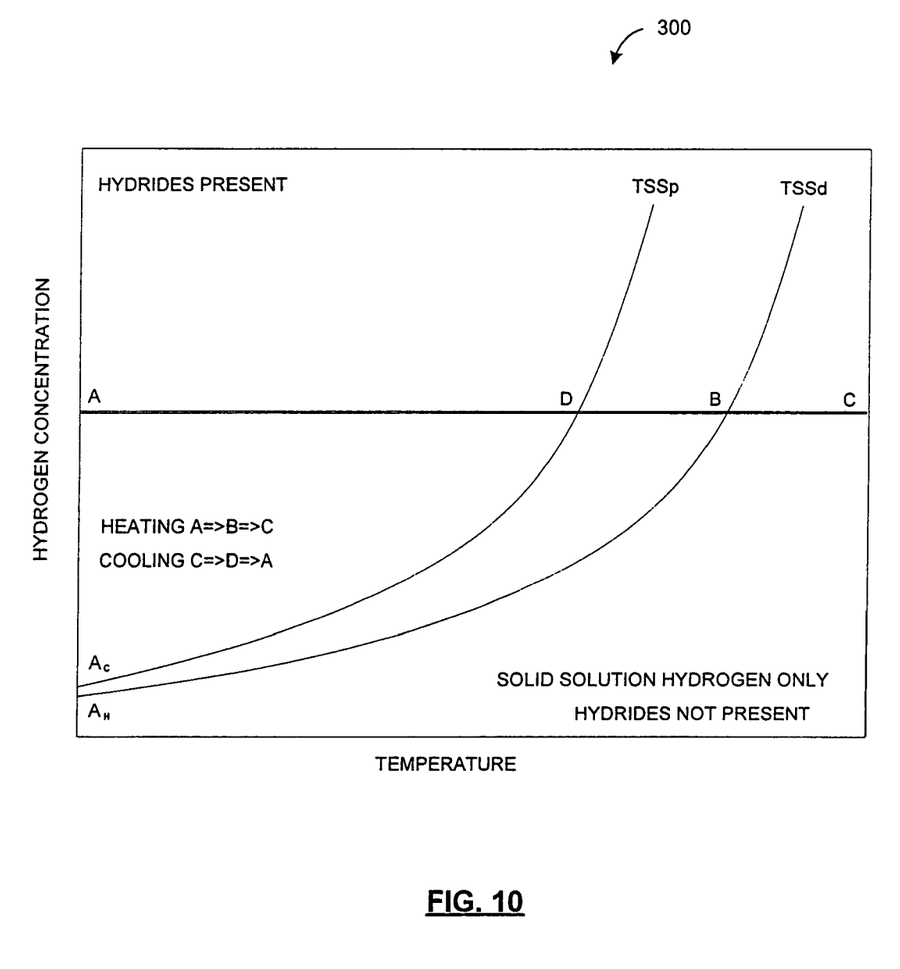
FIG. 10 shows a graph of hydrogen concentration versus temperature for an alloy.

Reference is first made to FIG. 10, which shows a graph 300 of hydrogen concentration versus temperature for an alloy. At point A on the graph 300, the alloy includes a mixture of hydride and solid solution hydrogen. As the alloy is heated, the hydrides dissolve and the solid solution hydrogen concentration follows a TSSd curve from $A_H$ to B. At point B, all the hydrides are dissolved into solid solution hydrogen. Further heating up to point C does not change the solid solution hydrogen concentration. Point B marks the TSSd temperature of dissolution for the alloy.

On cooling, all the hydrogen is in solid solution form until point D is reached, at which point hydrides begin to precipitate. This is the TSSp temperature of precipitation. As cooling continues, the hydrides grow and the solid solution hydrogen concentration decreases as it follows the TSSp curve from point D to point $A_C$.

In one embodiment, reactor pressure tubes are composed of a zirconium alloy, although the present invention is not limited to a method or apparatus for use in association with zirconium alloys or in the context of nuclear reactors. Other uses in the context of nuclear reactors include the testing of certain fuel claddings. Other mission critical components composed of other materials may be inspected using the method or apparatus of the present invention provided they exhibit the characteristics necessary, including the relationship of hydride concentration to TSSp and TSSd and to the presence hydrides. For example, titanium aircraft frames or titanium petrochemical pressure tubes may be analyzed according to the present invention.

The TSSp or TSSd for a particular reactor tube may be measured by detecting a discontinuity in the temperature coefficient of resistivity under conditions of controlled temperature increase or decrease. As the temperature of the tube is steadily increased, a discontinuity will be noted at a certain temperature corresponding to the TSSd, and once TSSd has been exceeded as the temperature is decreased, a discontinuity will be noted at a certain temperature corresponding to the TSSp.

The resistivity, also known as the electrical resistivity, of alloys is affected by the solid solution hydrogen concentration. The relationship may be modelled using the following equation:

$$\rho_T = \rho_o(1+\alpha(T)) + \rho_H C_H(T) \quad (1)$$

where $C_H(T)$ is the solid solution concentration of hydrogen as a function of temperature, $\rho_T$ is the total alloy resistivity, $\rho_H$ the effect of hydrogen on the resistivity, $\rho_O$ is the alloy base resistivity, and $\alpha(T)$ is the temperature coefficient of resistivity. As the TSSp or TSSd points are reached in the course of cooling or heating the alloy, a discontinuity is apparent in the temperature coefficient of resistivity.

Figure 1:
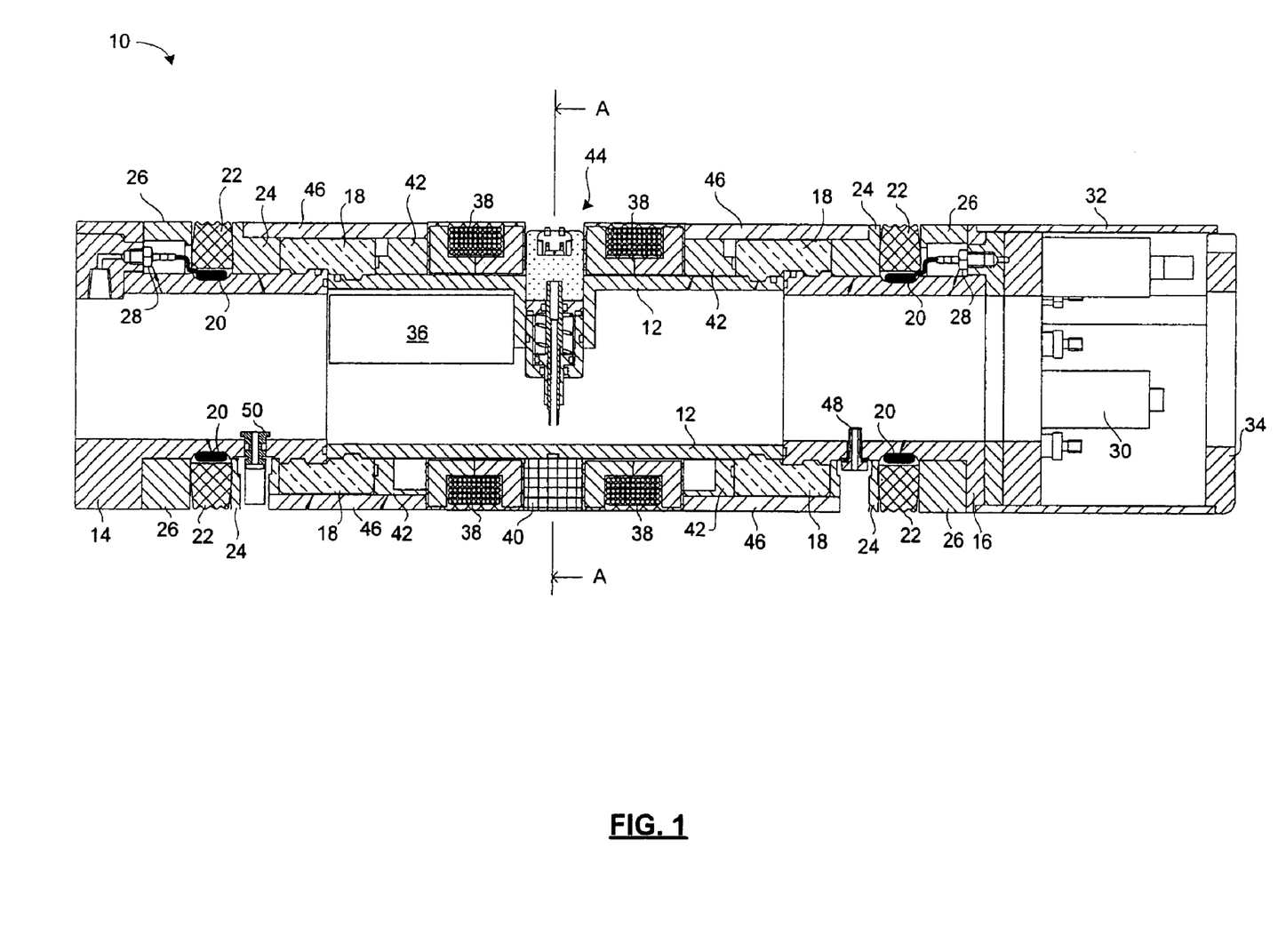
FIG. 1 shows a longitudinal cross-section view of a device for inspecting reactor pressure tubes, according to the present invention.
Figure 2:
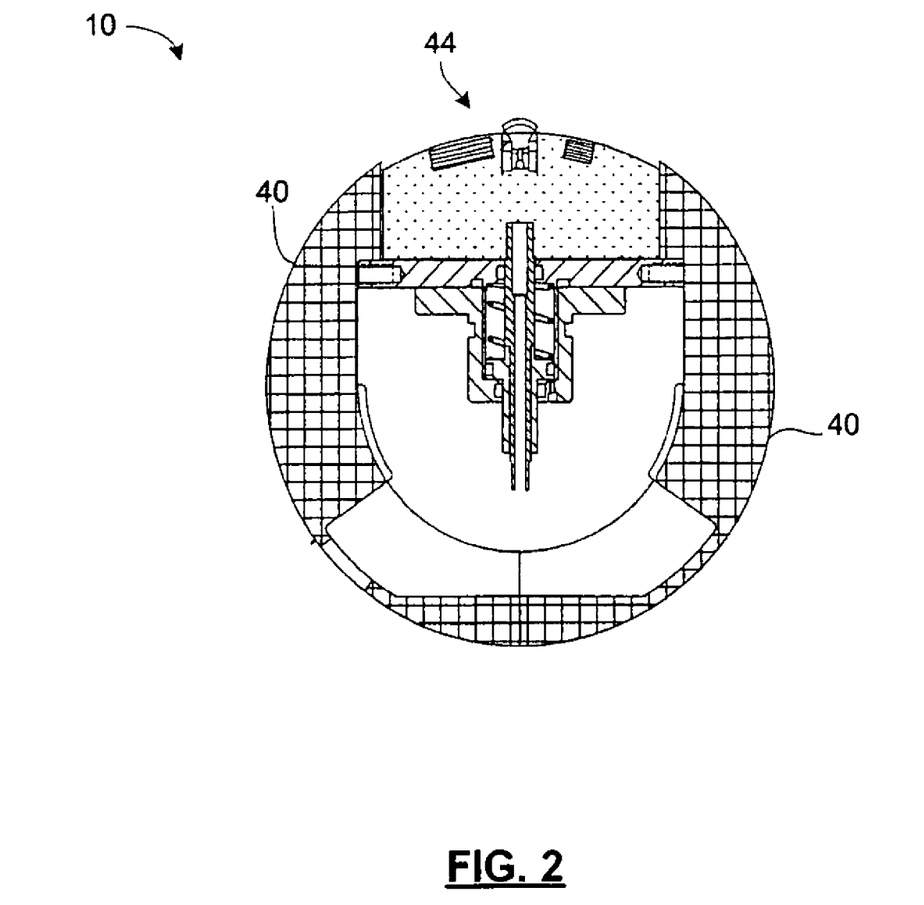
FIG. 2 shows a transverse cross-section view of the device of FIG. 1.

Reference is now made to FIGS. 1 and 2. FIG. 1 shows a longitudinal cross-section view of a device 10 for inspecting reactor pressure tubes. FIG. 2 shows a transverse cross-section view of the device 10 along the line A-A.

The device 10 includes a centre tube 12, a front module housing 14, and a rear module housing 16. The centre tube 12 is coupled to the front module housing 14 and to the rear module housing 16 using split clamps 18. The centre tube 12, front module housing 14, and rear module housing 16 provide the device 10 with a cylindrical shape.

Both the front module housing 14 and the rear module housing 16 include a bladder 20 and a seal 22. The bladders 20 and the seals 22 encircle the front and rear module housings 14, 16, and are held in place with inner retaining clamps 24 and outer retaining clamps 26. The bladders 20 are each coupled to a respective spigot 28. The spigots 28 are coupled to a gas supply for inflating and deflating the bladders 20. The inflation of the bladders 20 urges the seals 22 outward, pressing them radially against the inner surface of a tube under inspection.

The rear module housing 16 includes a valve manifold 30 for supplying gas to the spigots 28. A shroud 32 and a backplate 34 protect the valve manifold 30.

The centre tube 12 houses a resonant capacitor assembly 36 that is used to power a set of induction coils 38 located on the exterior of the centre tube 12. The induction coils 38 are mounted in place on the exterior of the centre tube 12 using an inner spacer 40 and outer spacers 42.

The centre tube 12 also houses an eddy current probe assembly 44 centered between the induction coils 38, as is further described below.

The exterior of the device 10 between the two seals 22 is encased by thermal shields 46 to protect it from the heat generated by the induction coils 38. The shields 46 also reduce the amount of heat lost from the pressure tube through the tool body.

Figure 3:
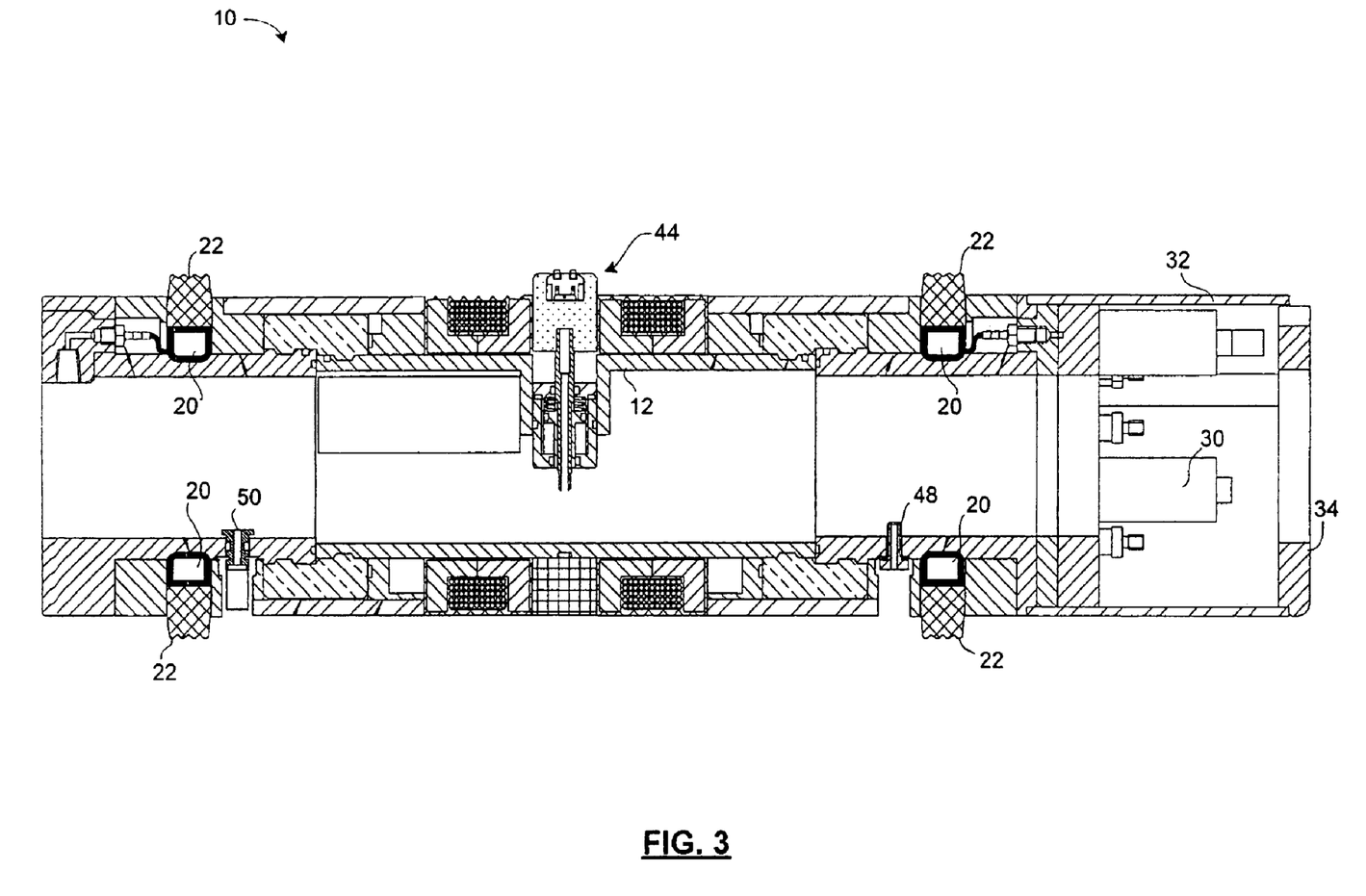
FIG. 3 shows a longitudinal cross-section view of the device when its bladders are inflated.
Figure 4:
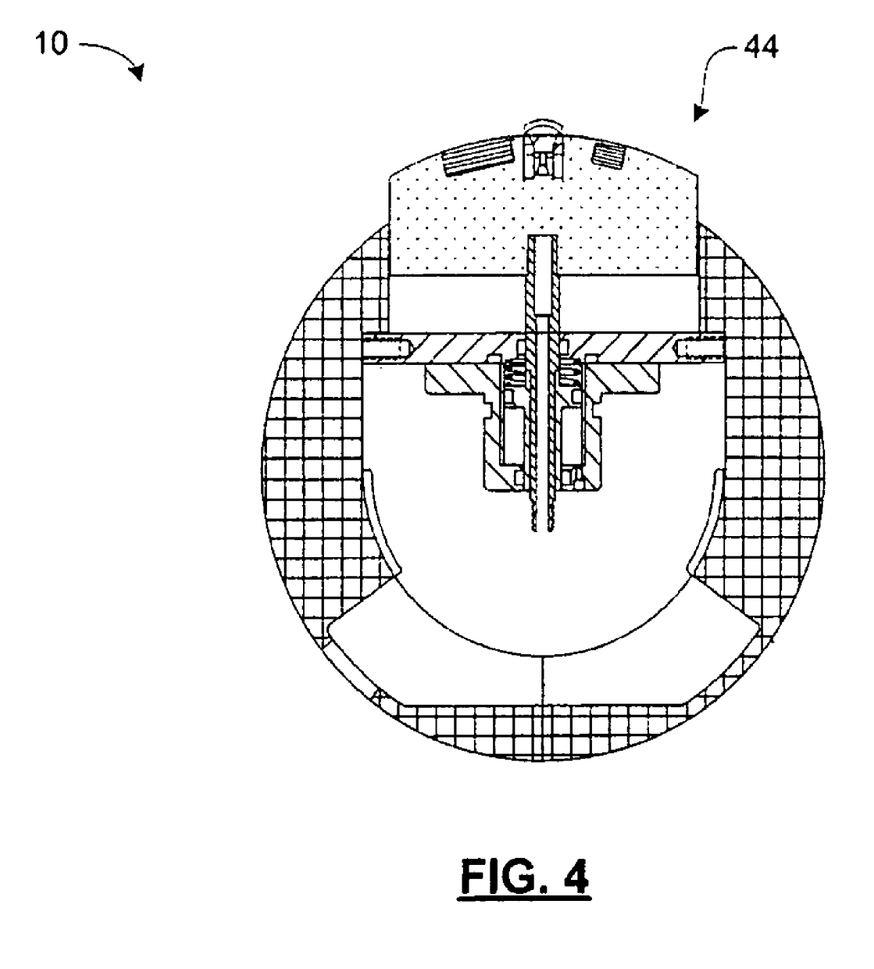
FIG. 4 shows a transverse cross-section view of the device of FIG. 3.

Reference is now made to FIGS. 3 and 4, which show longitudinal and transverse cross-section views of the device 10, respectively, when the bladders 20 are inflated. It will be noted from the Figures that the seals 22 have been pushed outwards by the inflated bladders 20.

The eddy current probe assembly 44 has also been deployed, and can be seen protruding radially outwards from the cylindrical surface of the device 10. When the seals 22 are urged outwards against the interior surface of a reactor pressure tube under analysis, then the eddy current probe assembly 44 may be deployed to test the reactor pressure tube, in accordance with the testing procedure describe below. In one embodiment, the eddy current probe assembly 44 is deployed through pneumatic pressure using gas supplied by the valve manifold 30. The gas supplied by the valve manifold 30 for operating the bladders 20 and the eddy current probe assembly 44 may be any inert gas and, in one embodiment, is nitrogen.

Referring now to FIGS. 1 and 3, the device 10 further includes a gas injection port 48 for injecting gas into the sealed section formed within the reactor pressure tube by deployment of the seals 22 against the interior surface of the tube. The water is displaced by the gas through a slot at the bottom of the seal 22. The device 10 also includes a water level sensor 50 for detecting the presence of water in the sealed section.

Figure 5:
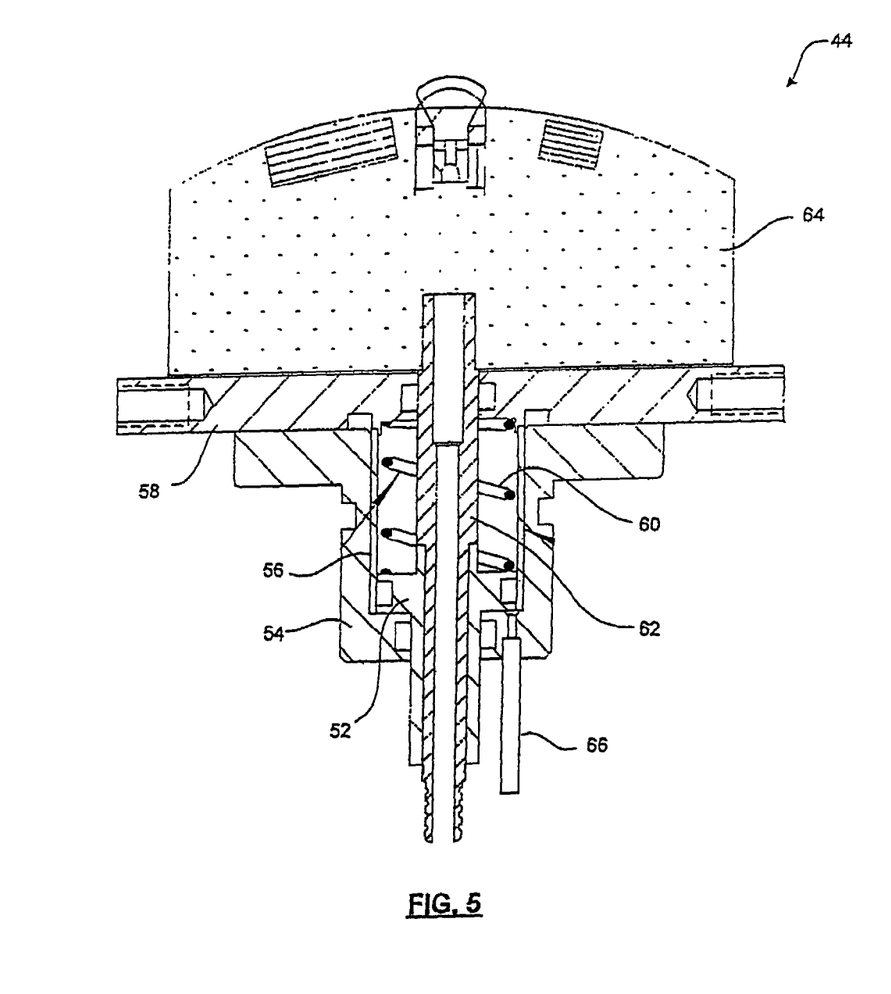
FIG. 5 shows a cross-sectional view of an eddy current probe assembly, according to the present invention.

Reference is next made to FIG. 5, which a cross-sectional view of the eddy current probe assembly 44. In order to retract the probe sensors during storage and initial positioning of the device 10 and to deploy the probe sensors once the device 10 is in place, the eddy current probe assembly 44 incorporates a reciprocating mechanism. In one embodiment, the reciprocating motion is achieved through a pneumatic assembly. The pneumatic assembly includes a piston 52 within a cylinder body 54. The interior of the cylinder body 54 is lined with a cylinder sleeve 56. The cylinder body 54 is mounted to a top plate 58 having an opening concentric with the cylinder body 54. A spring 60 biases the piston 52 into a retracted state. Through pneumatic pressure, the piston 52 may be pushed upwards in the cylinder body 54, compressing the spring 60. In one embodiment, the pressure is supplied through a gas inlet tube 66 in communication with the interior of the cylinder body 54 and having an opening proximate the underside of a flange on the piston 52.

The piston 52 includes a hollow shaft that accommodates a probe stem 62. The probe stem 62 is also hollow, so as to contain the wiring to connect the probe sensors to electronics within the device 10. The probe stem 62 extends through the piston 52 and up through the top plate 58 where it is coupled to a probe body 64. Accordingly, when the piston 52 is in its deployed position, the probe body 64 and probe stem 62 are extended outwards from the top plate 58. The probe body 64 features a curved outer surface designed to press flush against the interior surface of a reactor pressure tube of a known diameter.

Figure 6:
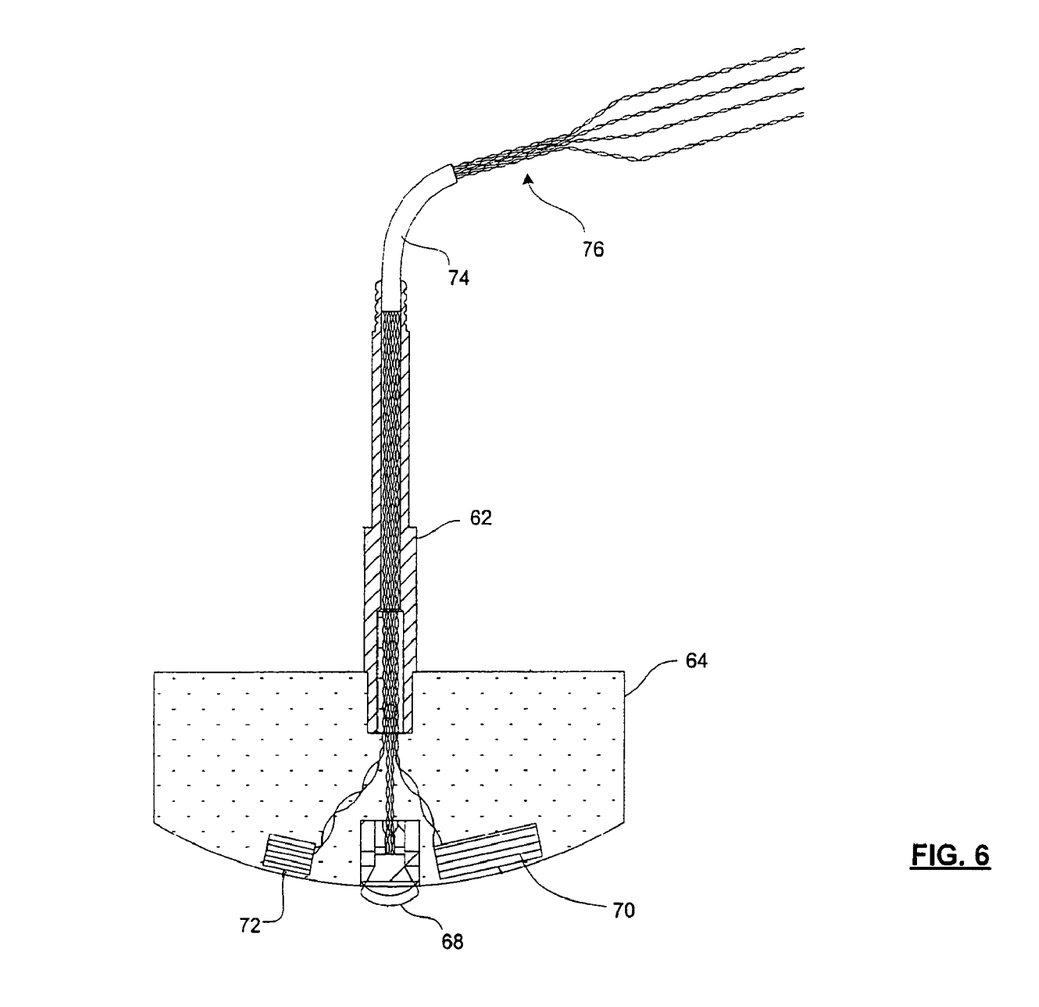
FIG. 6 shows a cross-sectional view of a probe body and probe stem from the eddy current probe assembly of FIG. 5.

Reference is now made to FIG. 6, which shows a cross-sectional view of the probe body 64 and probe stem 62. The probe body 64 includes a set of sensors for measuring the resistivity changes within a reactor pressure tube and the associated temperatures. In one embodiment, the probe body 64 includes a dual thermocouple probe 68. The dual thermocouple probe 68 is centered within the curved outer surface of the probe body 64.

On either side of the dual thermocouple probe 68 are a transmit coil 70 and a receive coil 72. These two coils 70, 72 are designed to induce eddy currents in the body of the pressure tube under evaluation. In one embodiment, the coils 70, 72 operate at 8 kHz.

The dual thermocouple probe 68, the transmit coil 70, and the receive coil 72 are all encapsulated within the probe body 64 so as to enhance the ruggedness of the eddy current probe assembly 44. In one embodiment, the probe stem 62 is manufactured from titanium to reduce stray eddy current effects.

Wiring 76 is attached to the thermocouple probe 68, the transmit coil 70, and the receive coil 72 and passes through the probe body 64 and into the probe stem 62. The wiring 76 extends through the probe stem 62 and into the interior of the centre tube 12 (FIG. 1) of the device 10. The wiring 76 includes a wire pair for each of the coils 70, 72 and two wire pairs for the thermocouple probe 68. The four wire pairs are polyimide coated. The eddy current probe assembly 44 may include a glass sleeve 74 to protect the wiring 76 as it exits the end of the probe stem 62. The wiring 76 may lead to a connector within the device 10. At this internal connection, the thermocouple wires may become regular copper wires and there may be a need to measure the temperature at this point. This temperature may be used as the cold junction temperature for final temperature calculations. In one embodiment, this is implemented using a 1000 Ohm platinum film RTD. The connector couples to a corresponding connector that is coupled to cabling that passes out of the device 10 and down the pressure tube.

The probe body 64 may be moulded to produce a single solid piece encapsulating the wiring 76, the thermocouple probe 68, the coils 70, 72, and the probe stem 62. In one embodiment, the probe body 64 is manufactured from an alumina filled high temperature epoxy made from Stycast 2764FT, produced by Emerson & Cumming Inc. of Massachusetts. The probe body 64 includes a single thin glass cloth covering the faces of the coils 70, 72 so as to protect them from wear. The thin class cloths may by moulded into the probe body 64 and may, for example, have a thickness of 0.005 inches. This allows the coils 70, 72 to remain as close to the probe face as possible while still being encapsulated and protected.

Figure 7:
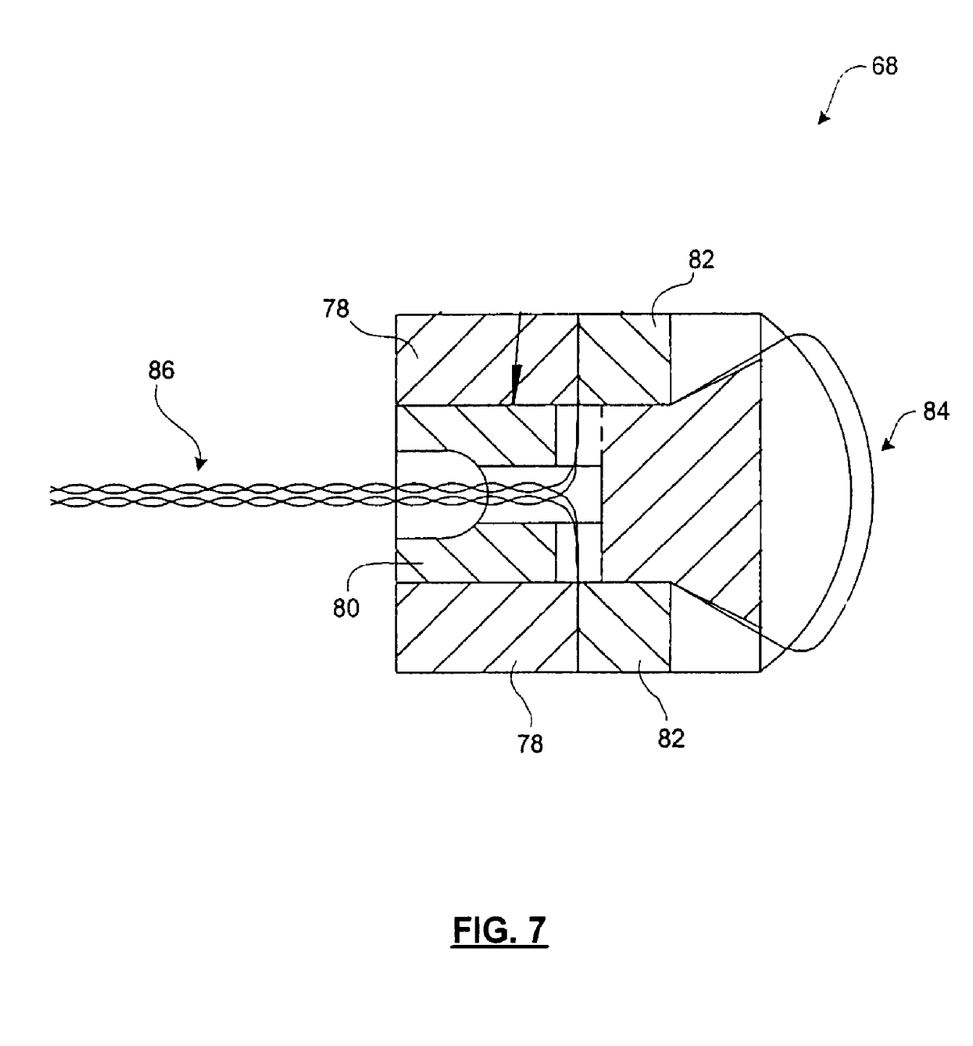
FIG. 7 shows a cross-sectional view of a thermocouple probe, according to the present invention.

Reference is now made to FIG. 7, which shows a cross-sectional view of the thermocouple probe 68. The thermocouple probe 68 includes main body pieces 78, 80, and 82. The main body pieces 78, 80, and 82 are chosen from a material having a low thermal conductivity so as to minimize heat flow through the material. Excessive heat flow could negatively impact the accuracy of the temperature measurement. In one embodiment, the main body pieces are machined from Vespel™, a polyimide polymer.

The thermocouple probe 68 also includes two type E thermocouple strips 84, each having its dissimilar metal junction centered with regard to the axis of the thermocouple probe 68. The strips 84 are welded to small diameter type E polyimide coated wires 86.

Once the thermocouple probe 68 is assembled, it is tested and a temperature correction table is developed based upon the testing. The thermocouple probe 68 may then be incorporated into the probe body 64 (FIG. 6), which, in turn, is incorporated into the eddy current probe assembly 44 (FIG. 5).

Figure 8:
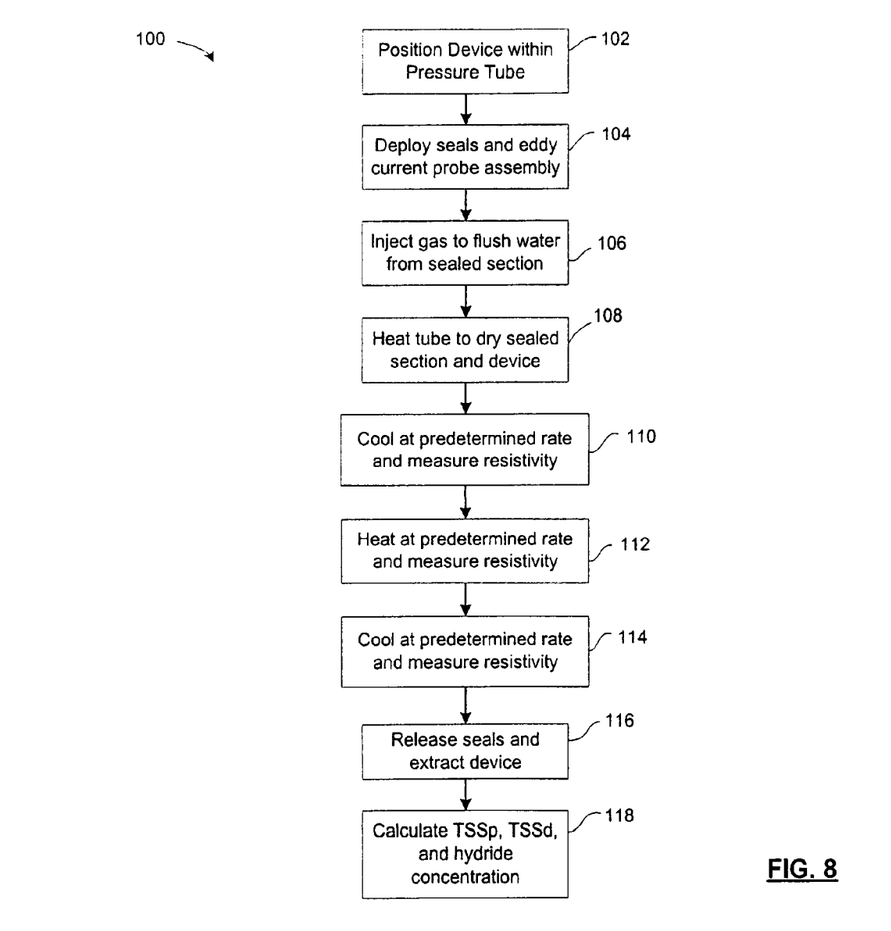
FIG. 8 shows a flowchart of a method of determining TSS temperature in a reactor pressure tube, according to the present invention.

The operation of the device 10 will now be described with reference to FIG. 8, which shows a flowchart of a method 100 of determining the TSS temperature using the device 10 according to the present invention.

The method 100 begins in step 102 with the insertion of the device 10 into a zirconium pressure tube and the positioning of the device 10 in the appropriate section of the tube where testing is to be conducted. In a preferred embodiment, the positioning of the eddy current probe is at the top of the pressure tube. In step 104, the section is sealed by inflating the bladders 20 (FIG. 3) to urge the seals 22 (FIG. 3) radially outwards against the interior surface of the tube. This step results in isolating the interior volume of the tube between the two seals 22. Also in step 104, the eddy current probe assembly 44 (FIG. 3) is deployed through pneumatic pressure to urge the curved outer surface of the probe body 64 (FIG. 5) against the interior surface of the tube, thereby bringing the thermocouple probe 68 (FIG. 6) into contact with the tube.

Under normal cold shutdown conditions, the pressure tube is filled with flowing water at a temperature of under 40 degrees Celsius. Once sealed the flow is diverted through the center of the device 10. This flow should not be reduced in order to prevent overheating of any fuel still present in the channel. The remaining isolated water must be flushed from the sealed volume between the seals 22 in order to control the heating and cooling cycles. Therefore, in step 106 the valve manifold 30 (FIG. 3) injects gas through the gas injection port 48 (FIG. 3) to flush the water from the sealed volume. In one embodiment, the gas is nitrogen, although any inert gas may be used. The water escapes through a small hole located at the bottom of the tool in one of the seals 22. The water level is evaluated by the water level sensor 50 (FIG. 3) via heat and gas pressure.

Once the water has been flushed from the sealed volume, the induction coils 38 (FIG. 1) driven by a 16 kHz power signal are used to heat the sealed section of pressure tube so as to dry out the tube and the eddy current probe assembly 44 in step 108. The induction coils 38 are powered by the resonant capacitor assembly 21 (FIG. 1). The temperature of the sealed section of the pressure tube is raised to approximately 300 degrees Celsius at a rate of about 20 degrees per minute. The device 10 is protected from the increasing temperatures through the thermal shields 46 on the exterior of the device 10 in the region between the seals 22. The water in the pressure tube on the other sides of the seals 22 reduces the temperature at the seals 22, preventing damage to them. The heating of the pressure tube ensures that all hydrides are dissolved. The steps flushing of water from the sealed volume in step 106 and the heating of tube to dry the device 10 and the tube in step 108 may be referred to as preconditioning.

In step 110, the pressure tube is allowed to cool at a predetermined rate which, in one embodiment, is 10 degree Celsius per minute. The tube is permitted to cool to about 70 degrees Celsius. During this cooling step, the transmit and receive coils 70, 72 induce eddy currents in the pressure tube and thereby measure the resistivity of the tube during the cooling process. This data is later used, in conjunction with the temperature data recorded by the thermocouple probe 68 (FIG. 6), to detect the TSSp temperature for the pressure tube. As the pressure tube cools, it will reach a point at which the dissolved hydrides begin to precipitate (the TSSp temperature), which results in the discontinuity in the temperature coefficient of resistivity. The cooling rate should be the same as, or faster than, the heating rate of the subsequent step in order to precipitate new hydrides with a known smaller given size. This improves the accuracy of the subsequent heating cycle which determines the TSSd temperature.

After the pressure tube is cooled to about 70 degrees Celsius, then in step 112 the tube is re-heated at a predetermined rate which, in one embodiment, is 10 degrees Celsius per minute. The tube is re-heated up to approximately 300 degrees Celsius. The re-heating causes the precipitated hydrides to dissolve at a certain temperature: the TSSd. The transmit and receive coils 70, 72 collect electrical resistivity data during the heating process to identify the discontinuity corresponding to the TSSd temperature.

In step 114, the tube is again allowed to cool to about 70 degrees Celsius, as in step 110, and another measurement of TSSp is obtained using the eddy current probe assembly 44. This second measurement of TSSp may be obtained for greater accuracy, but it may be omitted. The cooling ramp of this step may cool the tube to approximately 100 degrees Celsius.

Once the tube has cooled sufficiently, in step 116 the seals 22 and the eddy current probe assembly 44 are retracted by releasing the pressurized gas into the fuel channel via the valve manifold 30.

The method 100 then includes a step 118 of calculating the TSSp and TSSd based upon the data recorded by the thermocouple probe 68 and the induction coils 70, 72. Using the TSSp and the TSSd, the concentration of hydrogen in the section of tube under test may be determined using an appropriate Arrhenius relationship.

Figure 9:
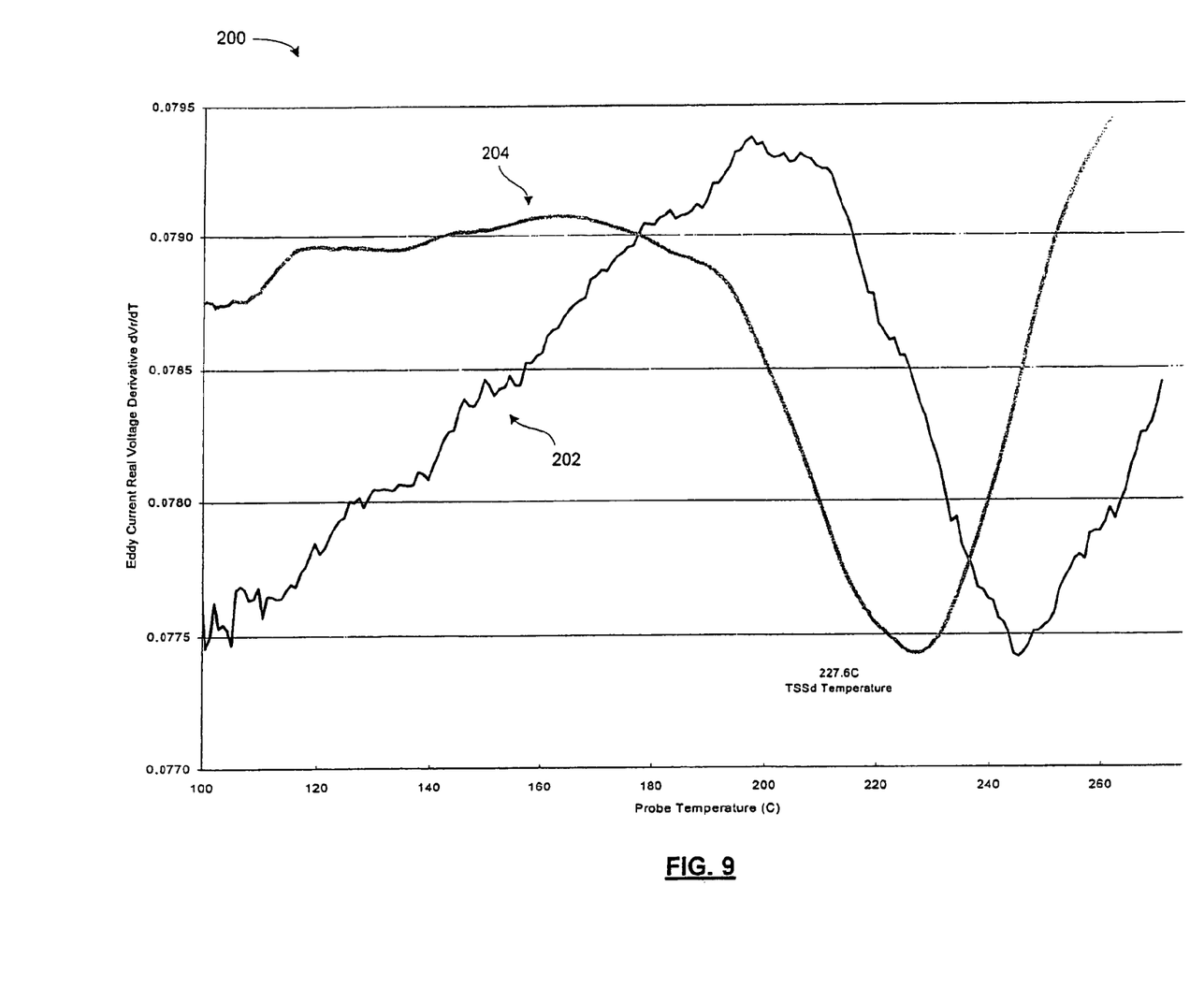
FIG. 9 shows a graph of eddy current real voltage derivative, and its derivative, versus temperature.

Reference is now made to FIG. 9, which shows a graph 200 of the eddy current real voltage derivative and its second derivative versus temperature. The graph 200 includes a first line 202 representing a magnified view of the temperature coefficient of resistivity for the pressure tube with respect to temperature. The first line 202 exhibits a steady rise due to increasing amounts of hydrogen dissolving in the zirconium matrix. Once the last amount of hydride dissolves, the first line 202 exhibits a sharp discontinuity at the TSSd temperature, which in this case is 227.6 degrees Celsius.

The graph includes a second line 204 representing the derivative of the first line 202. The minimum value of the second line 204 at 227.6 degrees Celsius identifies the discontinuity in the first line 202.

The precipitation event is similar in shape and behaviour.

The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method of inspecting reactor pressure tubes, comprising the steps of:
    (a) sealing a section of the reactor pressure tube;
    (b) initiating a temperature change within the reactor pressure tube at a predetermined rate;
    (c) measuring changes in the electrical resistivity of the reactor pressure tube in relation to the temperature change; and
    (d) determining a terminal solid solubility temperature of the reactor pressure tube from the measured changes in the electrical resistivity.

2. The method claimed in claim 1, further including a step of preconditioning the reactor pressure tube prior to said step of initiating, said step of preconditioning including heating said sealed section of reactor pressure tube.

3. The method claimed in claim 2, wherein said step of preconditioning includes injecting inert gas into said sealed section of reactor pressure tube to flush any fluids from said sealed section prior to said step of heating.

4. The method claimed in claim 1, wherein said step of initiating a temperature change includes cooling said sealed section of the reactor pressure tube at a first predetermined rate.

5. The method claimed in claim 4, wherein said step of initiating includes a subsequent step of re-heating said sealed section of the reactor pressure tube at a second predetermined rate.

6. The method claimed in claim 5, wherein said step of initiating includes a further subsequent step of re-cooling said sealed section of the reactor pressure tube at a third predetermined rate.

7. The method claimed in claim 4, wherein said first predetermined rate is 10 degrees Celsius per minute.

8. The method claimed in claim 5, wherein said second predetermined rate is 10 degrees Celsius per minute.

9. The method claimed in claim 1, wherein said step of measuring includes inducing eddy currents in the reactor pressure tube.

10. The method claimed in claim 1, wherein said step of determining further includes determining a hydrogen concentration from said terminal solid solubility temperature using an appropriate Arrhenius relationship.

11. The method claimed in claim 1, wherein said terminal solid solubility temperature includes a terminal solid solubility temperature of precipitation.

12. The method claimed in claim 1, wherein said terminal solid solubility temperature includes a terminal solid solubility temperature of dissolution.

13. The method claimed in claim 1, wherein said step of determining a terminal solid solubility temperature includes identifying a discontinuity in a temperature coefficient of resistivity from said measured changes in resistivity.

* * * * *